(12) United States Patent
Lia et al.

(10) Patent No.: US 9,220,422 B2
(45) Date of Patent: Dec. 29, 2015

(54) BLOOD PRESSURE SLEEVE

(71) Applicant: Welch Allyn, Inc., Skaneateles Falls, NY (US)

(72) Inventors: Raymond A. Lia, Auburn, NY (US); Robert L. Vivenzio, Auburn, NY (US); Eric Andreassen, Syracuse, NY (US); Daniel Sivilich, Syracuse, NY (US); Jeffrey J. Perkins, Tully, NY (US); Michael T. McMahon, Syracuse, NY (US); Chris R. Roberts, Skaneateles, NY (US); Richard A. Tamburrino, Auburn, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 506 days.

(21) Appl. No.: 13/681,217

(22) Filed: Nov. 19, 2012

(65) Prior Publication Data

US 2014/0142446 A1 May 22, 2014

(51) Int. Cl.
*A61B 17/00* (2006.01)
*A61B 5/022* (2006.01)

(52) U.S. Cl.
CPC .................................. *A61B 5/02233* (2013.01)

(58) Field of Classification Search
CPC ...... A61B 5/02; A61B 5/022; A61B 5/02208; A61B 5/0225; A61B 5/02233; A61B 2017/00858; A61B 2017/00845; A61B 2017/0084; A61B 17/135; A61B 7/02; A61B 7/022; A61B 7/02208; A61B 7/02233; A61B 7/0225; A61F 5/34; A61F 2250/0021; A61M 2025/0062; A61M 2025/1088

USPC .......... 606/201–203; 600/490, 491, 495, 496, 600/499

See application file for complete search history.

(56) References Cited

U.S. PATENT DOCUMENTS

| | | |
|---|---|---|
| 1,106,341 A | 8/1914 | Bristol |
| 1,328,876 A | 1/1920 | Hill |

(Continued)

FOREIGN PATENT DOCUMENTS

| | | |
|---|---|---|
| CA | 2100854 | 1/1994 |
| DE | 591564 | 1/1934 |

(Continued)

OTHER PUBLICATIONS

Stick-slip phenomenon. Dec. 15, 2007. <http://en.wikipedia.org/wiki/Stick-slip_phenomenon>.*

(Continued)

*Primary Examiner* — Todd E Manahan
*Assistant Examiner* — Charles Wei

(57) ABSTRACT

A blood pressure sleeve includes a first sheet having a top side and a bottom side and a second sheet having a top surface and a bottom surface. The second sheet is attached to the first sheet and defines an inflatable portion, the first and second sheets each having a fluid impermeable surface. The inflatable portion includes an opening sized for receiving a port that interconnects the exterior of the sleeve with the interior of the inflatable portion and in which the first sheet includes a slotted portion opposite the port and aligned therewith to receive the port when the sleeve is wrapped about the limb of a patient, and in which at least a portion of the wrapped cuff is treated to reduce frictional effects.

29 Claims, 13 Drawing Sheets

(56) References Cited

U.S. PATENT DOCUMENTS

| | | | |
|---|---|---|---|
| 1,377,032 A | 5/1921 | Starling et al. | |
| 1,729,297 A | 9/1929 | Stewart | |
| 2,087,494 A | 7/1937 | Annin | |
| 2,341,137 A | 2/1944 | Damron | |
| 2,564,669 A | 8/1951 | Brady | |
| 2,618,269 A * | 11/1952 | Baum et al. | 606/202 |
| 2,636,394 A | 4/1953 | Melchior | |
| 2,678,040 A | 5/1954 | Poole et al. | |
| 2,714,379 A | 8/1955 | Raines | |
| 1,740,181 A | 11/1955 | Clark | |
| 3,279,459 A | 10/1966 | Schenker | |
| 3,473,525 A | 10/1969 | Hanafin | |
| 3,606,880 A | 9/1971 | Ogle, Jr. | |
| 3,633,567 A | 1/1972 | Sarnoff | |
| 3,635,214 A | 1/1972 | Rand et al. | |
| 3,659,592 A | 5/1972 | Natkanski | |
| 3,756,239 A | 9/1973 | Smythe | |
| 3,757,772 A | 9/1973 | Goldblat et al. | |
| 3,760,795 A | 9/1973 | Adelhed | |
| 3,773,036 A | 11/1973 | Weyer | |
| 3,797,315 A | 3/1974 | Halpern | |
| 3,805,618 A | 4/1974 | Csaposs et al. | |
| 3,874,242 A | 4/1975 | Csaposs et al. | |
| 3,906,937 A | 9/1975 | Aronson | |
| 3,977,393 A | 8/1976 | Kovacic | |
| D244,879 S | 6/1977 | Manno | |
| 4,036,061 A | 7/1977 | Speidel | |
| 4,036,216 A | 7/1977 | Ramsey, III | |
| 4,040,298 A | 8/1977 | Lee et al. | |
| 4,248,241 A | 2/1981 | Tacchi | |
| 4,255,970 A | 3/1981 | Van Pottleberg | |
| D269,905 S | 7/1983 | Tamm | |
| 4,501,271 A | 2/1985 | Clifton et al. | |
| 4,535,938 A | 8/1985 | Lindabury, Sr. | |
| 4,543,824 A | 10/1985 | Marterer | |
| 4,548,249 A | 10/1985 | Slaughterbeck | |
| 4,549,550 A | 10/1985 | Kami | |
| 4,605,010 A | 8/1986 | McEwen | |
| 4,653,506 A | 3/1987 | Romanovskaya | |
| 4,685,336 A | 8/1987 | Lee | |
| 4,726,382 A | 2/1988 | Boehmer et al. | |
| 4,726,686 A | 2/1988 | Wolf et al. | |
| 4,802,370 A | 2/1989 | EerNisse et al. | |
| 4,844,512 A | 7/1989 | Gahwiler | |
| 4,896,676 A | 1/1990 | Sasaki | |
| 4,920,971 A | 5/1990 | Blessinger | |
| 4,967,758 A | 11/1990 | Masciarotte | |
| 4,979,953 A | 12/1990 | Spence | |
| 5,003,981 A | 4/1991 | Kankkunen et al. | |
| 5,025,792 A | 6/1991 | Hon et al. | |
| 5,048,533 A | 9/1991 | Muz | |
| 5,101,830 A | 4/1992 | Duffy et al. | |
| 5,137,024 A | 8/1992 | Souma | |
| 5,179,957 A | 1/1993 | Williams | |
| 5,181,422 A | 1/1993 | Leonard et al. | |
| 5,220,925 A | 6/1993 | Hishida | |
| 5,228,448 A | 7/1993 | Byrd | |
| 5,251,646 A | 10/1993 | Bowen | |
| 5,275,444 A | 1/1994 | Wythoff | |
| 5,320,169 A | 6/1994 | Delatorre | |
| 5,392,782 A | 2/1995 | Garrett | |
| D356,155 S | 3/1995 | Caven | |
| 5,396,894 A | 3/1995 | Eide et al. | |
| 5,400,787 A | 3/1995 | Marandos | |
| 5,413,582 A | 5/1995 | Eaton | |
| 5,424,598 A | 6/1995 | Corbett | |
| 5,511,552 A | 4/1996 | Johnson | |
| 5,513,534 A | 5/1996 | Brechlbühl et al. | |
| 5,513,643 A | 5/1996 | Suite | |
| 5,540,714 A * | 7/1996 | Payne et al. | 606/201 |
| 5,626,142 A | 5/1997 | Marks | |
| 5,660,182 A | 8/1997 | Kuroshaki et al. | |
| 5,678,558 A | 10/1997 | Johnson | |
| 5,690,672 A | 11/1997 | Cohen | |
| 5,746,213 A | 5/1998 | Marks | |
| 5,753,821 A | 5/1998 | Chou | |
| 5,797,851 A | 8/1998 | Byrd | |
| 5,819,739 A | 10/1998 | Levavi et al. | |
| 5,882,515 A | 3/1999 | Lacy et al. | |
| 5,904,655 A | 5/1999 | Brackett | |
| 5,966,829 A | 10/1999 | Lia et al. | |
| 6,036,718 A | 3/2000 | Ledford et al. | |
| 6,082,170 A | 7/2000 | Lia et al. | |
| 6,095,983 A | 8/2000 | Wawro | |
| 6,120,458 A | 9/2000 | Lia et al. | |
| 6,149,600 A | 11/2000 | Poor-Ketchum | |
| 6,152,880 A | 11/2000 | Okada | |
| 6,168,566 B1 | 1/2001 | Lia et al. | |
| 6,189,558 B1 | 2/2001 | Traylor | |
| 6,213,953 B1 | 4/2001 | Reeves | |
| 6,234,972 B1 | 5/2001 | Lia et al. | |
| 6,245,023 B1 | 6/2001 | Clemmons | |
| 6,245,024 B1 | 6/2001 | Montagnino et al. | |
| 6,344,025 B1 | 2/2002 | Inagaki et al. | |
| 6,346,084 B1 | 2/2002 | Schnell et al. | |
| 6,364,843 B1 | 4/2002 | Lightle | |
| 6,394,977 B1 | 5/2002 | Taylor et al. | |
| 6,422,086 B1 | 7/2002 | Dromms et al. | |
| 6,475,153 B1 | 11/2002 | Khair et al. | |
| 6,481,291 B1 | 11/2002 | Lia et al. | |
| 6,506,162 B1 | 1/2003 | Tseng | |
| 6,525,238 B2 | 2/2003 | Corrales | |
| 6,551,249 B2 | 4/2003 | Ashida et al. | |
| 6,578,428 B1 | 6/2003 | Dromms et al. | |
| 6,615,666 B1 | 9/2003 | Lia et al. | |
| 6,616,666 B1 | 9/2003 | Michelson | |
| 6,682,547 B2 | 1/2004 | McEwen et al. | |
| 6,746,406 B2 | 6/2004 | Lia et al. | |
| 6,796,186 B2 | 9/2004 | Lia et al. | |
| D532,519 S | 11/2006 | Aujla et al. | |
| 7,153,270 B2 * | 12/2006 | Sano et al. | 600/499 |
| 7,311,670 B2 | 12/2007 | Just et al. | |
| D568,478 S | 5/2008 | Karla et al. | |
| 7,429,245 B2 | 9/2008 | Whitaker et al. | |
| 7,722,542 B2 | 5/2010 | Lia et al. | |
| 7,780,698 B2 | 8/2010 | McEwen et al. | |
| 8,147,417 B2 | 4/2012 | Gavriely | |
| 2001/0005777 A1 | 6/2001 | Nakagawa et al. | |
| 2002/0099297 A1 | 7/2002 | Nakagawa et al. | |
| 2002/0156382 A1 | 10/2002 | Freund et al. | |
| 2003/0036690 A1 | 2/2003 | Geddes et al. | |
| 2003/0105487 A1 * | 6/2003 | Benz et al. | 606/201 |
| 2004/0049114 A1 | 3/2004 | Alesse | |
| 2004/0083816 A1 | 5/2004 | Lia et al. | |
| 2004/0092831 A1 | 5/2004 | Hood, Jr. | |
| 2004/0181156 A1 | 9/2004 | Kingsford et al. | |
| 2005/0131309 A1 * | 6/2005 | Gotz et al. | 600/491 |
| 2005/0171445 A1 | 8/2005 | Millay et al. | |
| 2006/0089668 A1 | 4/2006 | Warburton | |
| 2006/0217618 A1 | 9/2006 | Lia et al. | |
| 2006/0293600 A1 | 12/2006 | Wawro et al. | |
| 2007/0135836 A1 | 6/2007 | McEwen et al. | |
| 2007/0244506 A1 | 10/2007 | McEwen et al. | |
| 2008/0114320 A1 | 5/2008 | Beck et al. | |
| 2008/0119117 A1 * | 5/2008 | Nichols | 451/63 |
| 2008/0243010 A1 | 10/2008 | Kulik | |
| 2009/0171223 A1 | 7/2009 | McEwen et al. | |
| 2010/0089408 A1 | 4/2010 | McCaughey et al. | |
| 2010/0186752 A1 | 7/2010 | Rixon | |
| 2010/0298724 A1 * | 11/2010 | Vivenzio et al. | 600/490 |
| 2010/0298725 A1 * | 11/2010 | Vivenzio et al. | 600/490 |
| 2012/0150051 A1 | 6/2012 | Kinsley et al. | |

FOREIGN PATENT DOCUMENTS

| | | |
|---|---|---|
| DE | 2220233 | 11/1973 |
| EP | 0 591 564 A1 | 4/1994 |
| EP | 0 705 563 A1 | 4/1996 |
| EP | 1 992 281 | 11/2008 |
| FR | 2592297 | 7/1987 |
| GB | 740181 | 11/1955 |
| JP | 1101971424 | 7/1999 |
| JP | 2002-25318 | 9/2002 |
| WO | WO 00/22983 | 4/2000 |

(56) References Cited

FOREIGN PATENT DOCUMENTS

| WO | WO 00/40941 | 7/2000 |
| WO | WO 02/26128 A2 | 4/2002 |
| WO | WO 2007/035271 A1 | 3/2007 |
| WO | WO 2007/116588 A1 | 10/2007 |
| WO | WO 2007/125546 A1 | 11/2007 |
| WO | WO 2011/130020 A1 | 10/2011 |

OTHER PUBLICATIONS

Brandt, Jobst. Brake Squeal. May 11, 2001. <http://sheldonbrown.com/brandt/brake-squeal.html>.*

Chinese Office Action for CN 2501080022067.5; dated Dec. 3, 2014; 7 page.

Supplementary European Search Report for EP 06790195; Dated Oct. 30, 2009; 11 pages.

International Search Report and Written Opinion for PCT/US07/16828; dated Jan. 18, 2008; 5 pages.

International Search Report and Written Opinion for PCT/US06/34909; dated Feb. 5, 2007; 6 pages.

International Search Report and Written Opinion for PCT/US2011/053376; dated May 4, 2012; 7 pages.

International Search Report and Written Opinion for PCT/US2010/035062; dated Sep. 28, 2010; 16 pages.

International Search Report and Written Opinion for PCT/US2010/035065; dated Sep. 27, 2010; 16 pages.

"Plastics Plus, Inc. Biodegradable Solution PPI BD-0701"; Published Oct. 2008; 8 pages.

Welch Allyn DuraShock Integrated Aneroid Sphygmomanometer Operating Instruction Manual; 8 pages.

Alpert, et al., "The papercuff, a new disposable blood pressure cuff"; The American Journal of Cardiology; vol. 77; Mar. 1, 1966; 4 pages.

"Socket", The American Heritage Dictionary of the English Language; Houghton Mifflin Company; © 2003; Retrieved Nov. 7, 2007 from http://www.credoreference.com/entry/4133272; 1 page.

Vogt et al.; Oxo-biodegradable polyolefins show continued and increased thermal oxidative degradation after exposure to light; 2009; Polymer Degradation and Stability; vol. 94; pp. 659-663; 5 pages.

Wikipedia; Gender of connectors and fasteners at Wikipedia.org; pp. 1-11; 11 pages.

Bruno, E.A.; Automated sorting of plastics for recycling; 2006; p2pays.org; pp. 3 and 5-16; 13 pages.

* cited by examiner

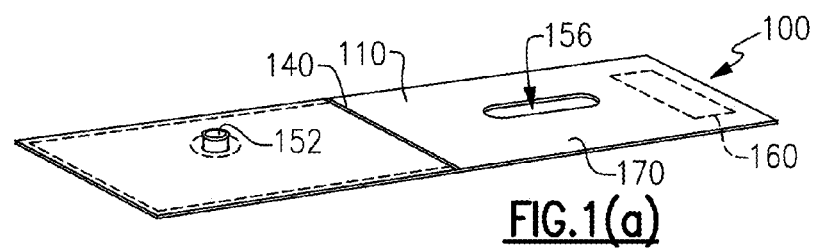
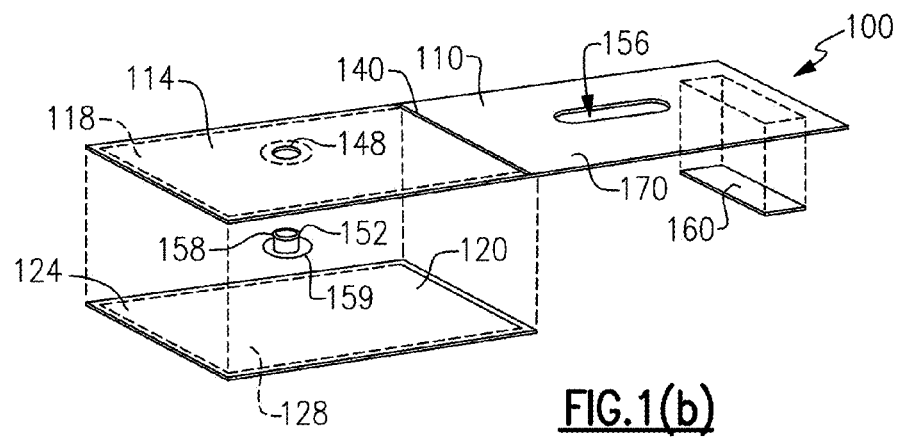

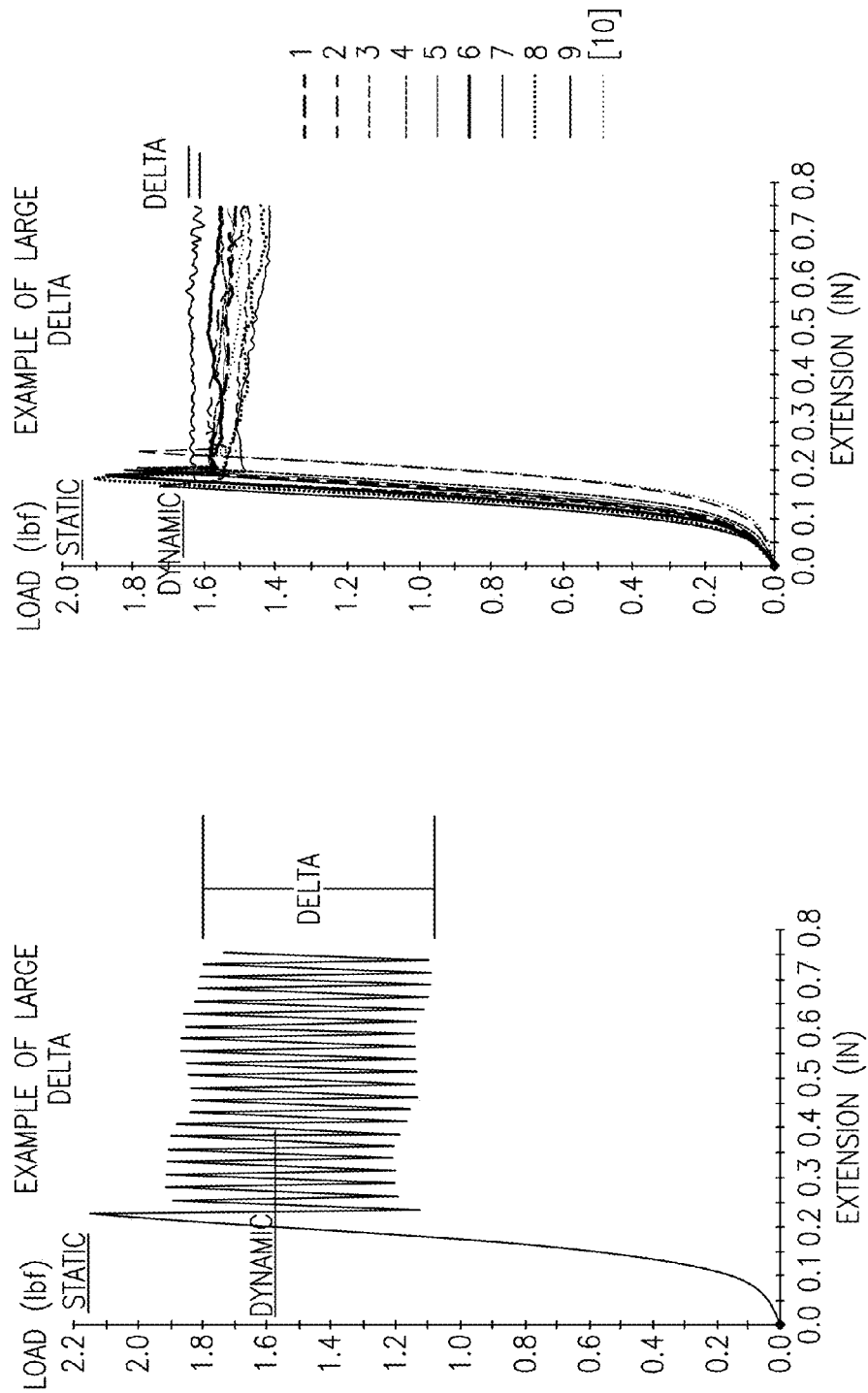

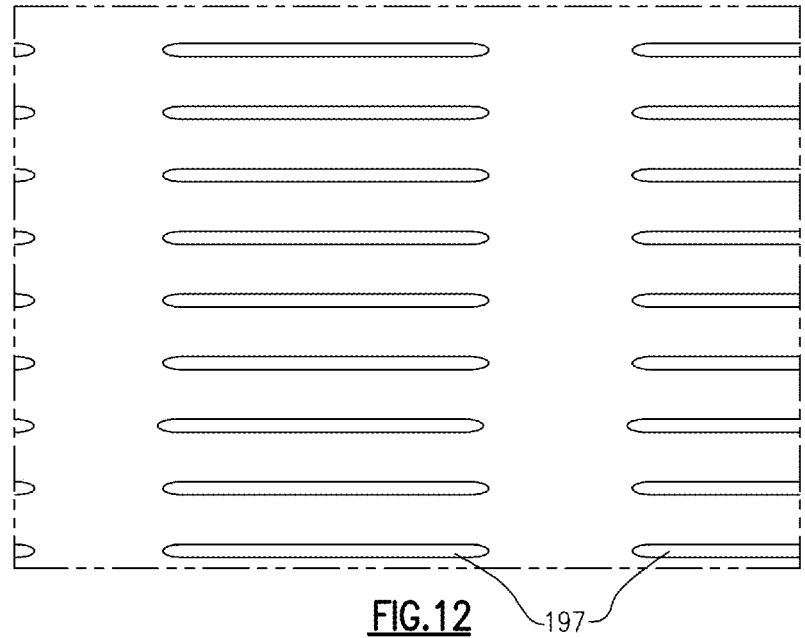
FIG.12 —197
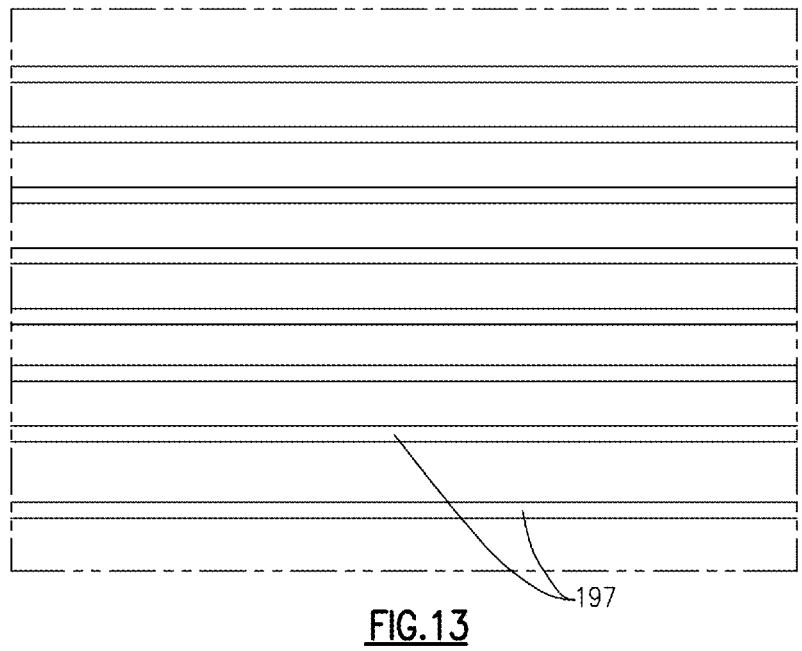
FIG.13 —197

BLOOD PRESSURE SLEEVE

TECHNICAL FIELD

This application relates generally to the field of diagnostic medicine and more specifically to a disposable or recyclable blood pressure sleeve or cuff that permits use of same with systems that measure blood pressure on either the inflate or the deflate portion of their measurement cycle.

BACKGROUND

Sphygmomanometers are commonly known and established medical diagnostic instruments used for measuring the blood pressure of a patient. In one well known version, a reusable cuff or sleeve made from fluid-impermeable materials is wrapped about the limb (e.g., arm or leg) of the patient. Various sized sleeves are made, depending upon the class (i.e., child, adult, neonatal) of the patient. Most sleeves of this type are defined by either a pair of planar sheets that are sealed together or are formed of a single sheet, the sleeve either having a contained bladder or an inflatable interior compartment. The sleeves further typically include hook and loop fasteners disposed at specific locations on opposing sides in order permit releasable and adjustable attachment to a patient, as well as removal therefrom. The bladder or interior inflatable compartment is inflated using pneumatic means, such as a pump, which is tethered to the cuff by means of a flexible hose attached to a barb that is provided on the exterior of the sleeve. Pressure variations in the sleeve can then be detected by a gage housing having a dial indicator that is attached to the cuff. In mechanical versions, the gage housing contains a movement mechanism having a pressure responsive element, such as a diaphragm, wherein pressure variations are imparted to the dial indicator on the gage housing, according to the well-known oscillometric technique. Electronic blood pressure measuring versions, which may or may not include a pump directly within the gage housing, are also known such as those manufactured and sold by Welch Allyn, Inc. and Omron Corporation, among others, the results being displayed for example, using an LCD. In these latter types of devices, either the oscillometric (pulsatile) or auscultory method of pressure measurement can be utilized, the latter being used in combination with a stethoscope or microphone.

These diagnostic instruments are repletely found in a doctor's office or within examination rooms found in a medical facility or hospital. With regard to a medical facility or hospital and depending upon the number of procedures that are performed on a patient during an examination or a typical hospital or urgent care facility visit, there are compelling reasons why a blood pressure sleeve should not be reused, for example, the potential for cross contamination of infectious fluids between patients, among others.

To that end, efforts have been made to create "single use" or "single patient" blood pressure cuffs that can be used either a single time or over the course of an entire hospital visit for a patient. Exemplary versions of these cuffs are described, for example, in U.S. Patent Application Publication No. 2010/0298725 A1 filed on Feb. 12, 2010, and entitled "Recyclable or Biodegradable Blood Pressure Cuff", U.S. Patent Publication No. 2010/0298724 A1, and entitled "Recyclable or Biodegradable Blood Pressure Cuff, filed on May 19, 2009, U.S. Patent Application Publication No. 2012/0150051 A1, entitled "Blood Pressure Cuff" and filed on Dec. 9, 2009, the entire contents of each of these documents being relied upon and incorporated by reference in their entirety. As to electronic blood pressure measuring apparatus, a detailed description of an exemplary embodiment of an electronic apparatus for the non-invasive measurement of blood pressure is presented in commonly owned U.S. Pat. No. 7,429,245, issued on Sep. 30, 2008, and entitled "Motion Management in a Fast Blood Pressure Measurement Device". This latter device advantageously measures blood pressure during inflation of the blood pressure sleeve as opposed to step-down deflation measurements, which are commonly known. As a result, measurement results can be obtained more expediently and with less anxiety for the patient, among other benefits.

The creation of an inexpensive single use or single patient blood pressure cuff can include fabrication from a single material, such as polyethylene or polypropylene, that promotes recyclability. According to one exemplary version, an inflatable portion is created between two sheets of a single type of material that are attached through welding or other securing means in which a fluid impermeable compartment is formed. A port or socket provided in an opening of the inflatable portion enables the attachment of pneumatic means, as previously described, to permit inflation. The inflatable compartment is initially and circumferentially wrapped about the limb (e.g., the arm) of the patient and an axially extending portion of the cuff is further wrapped about the inflatable portion, the axially extending portion of the cuff including a slotted portion that is sized to receive the extending port. These sleeves, as developed, function properly when used to take conventional blood pressure measurements during the step-down deflation phase of the measurement cycle. However and in attempting to reliably utilize cuffs of this type for measuring blood pressure during the inflation cycle, numerous problems have been encountered. One such problem is discussed in U.S. Patent Application Publication No. 2012/0150051 A1, relating to lobeing or pillowing of the inflatable portion or a bladder added to define an inflatable chamber, in which increases in inflation pressure can cause a lobed portion to undesirably "pop" or release during the inflation period.

In the course of developing single use or single patient cuffs, another problem that has been encountered involves a frictional "stick-slip" between sliding surfaces of the wrapped sleeve. In one version, the wrapped cuff includes a hook fastener portion at one end of an axial extending portion of the cuff opposite from the inflatable portion of the cuff that is preferably made from the same material as the remainder of the cuff. The hook fastener portion acts in concert with a non-woven side of the sleeve, the latter including a series of interlaced fibers that behave as loop fasteners when engaged by the hook fastener portion to act as closure means for the sleeve when wrapped. In the course of wrapping the sleeve about the inflatable portion and advancing the slotted portion to the port, the bottom surface of the axial extending portion of the sleeve is in sliding contact against the wrapped non-woven surface. It has been determined that the frictional interaction between these surfaces changes, for example, as the sleeve is inflated. To that end, the character of this cuff design is such that the static and dynamic coefficients of friction between the contacting surfaces vary. In addition, the dynamic coefficient of friction also varies on its own based on load, such as during inflation of the cuff. These changes produce a "stick then slip" characteristic, as opposed to a continuous and predictable inflating action of the wrapped cylinder, which can invariably introduce undesirable noise into the resulting measurement signal and affect overall accuracy.

Therefore, there is a need to create a disposable or recyclable blood pressure cuff design that can be advantageously used to reduce noise when the cuff is used, including during inflation. However and to date such incorporation has not been possible for numerous reasons, such as the above-noted frictional effects that are created by a single material wrappable cuff design.

SUMMARY

Therefore and according to one aspect, there is provided a blood pressure sleeve comprising a first sheet having a top surface and a bottom surface and a second sheet having a top surface and a bottom surface. The second sheet is attached to the first sheet and defines an inflatable interior portion between the bottom surface of the first sheet and the top surface of the second sheet. The inflatable interior portion includes an opening that receives a port fluidly interconnecting the interior of said inflatable portion with the exterior of said cuff. The first sheet includes an axial extension having a slotted portion aligned with the port such that the port can be fitted within the slotted portion when the sleeve is circumferentially wrapped about the limb of a patient wherein the top surface of the first sheet is defined by a nonwoven surface and the bottom surface is defined by a fluid impermeable surface, and in which at least one of the nonwoven and fluid impermeable surfaces of at least a portion of said first sheet is treated to reduce frictional effects between contacting top and bottom surfaces of the first sheet in a wrapped configuration.

According to one version, at least a portion of at least one of the contacting surfaces of the first sheet is treated such that at least one of the coefficient of static friction and the coefficient of dynamic friction between the contacting surfaces is increased from an untreated level. According to at least another version, at least a portion of at least one of the contacting surfaces of the first sheet is treated such that the differential between the static and dynamic frictional coefficients between the contacting surfaces is minimized. In yet another embodiment, at least a portion of at least one of said contacting surfaces of the first sheet is treated such that any typical variation in dynamic friction coefficient between the contacting surfaces is minimized.

According to at least one version, the fluid impermeable surface of the axial extension of the sleeve includes a hook fastener portion at one end opposite the inflatable portion and in which the non-woven surface of the first sheet is configured to adhere to the hook fastener portion when the sleeve is wrapped. The non-woven surface can be configured such that the hook fastener portion will not adhere to the non-woven surface of the sleeve after a predetermined number of uses.

According to at least one version, at least a portion of the fluid impermeable side of the axial extension is exfoliated. Preferably, the exfoliated portions of the axial extension of the sleeve are defined by a plurality of substantially parallel protrusions that are produced along the axial direction of the sleeve.

According to another embodiment, at least a portion of the first sheet is washed or wiped. Preferably, the entire sheet can be washed or wiped, such as prior to assembling the cuff. In another version, at least a portion of the first sheet can be heat-treated.

In another version, at least a portion of the fluid impermeable surface of the wrapped sleeve is defined by at least one surface pattern disposed thereon, the at least one surface pattern being applied by one of sanding, extruding, stamping, heating and welding. A surface texture is created that preferably produces an increase in surface roughness that enables the static coefficient of friction between the contacting surfaces to be increased. During inflation, this effect tends to minimize slippage between the wrapped surfaces and improves accuracy by reducing signal noise.

The area of treatment according to one embodiment extends between a seam defining the inflatable portion and the slotted portion. Alternatively, the area of treatment can extend between a seam defining the inflatable portion and the hook fastener portion. Other appropriate areas can be locally defined or the entirety of one or both surfaces can be treated.

According to another aspect, there is provided a method of manufacturing a blood pressure sleeve comprising the steps of: providing a first sheet having a top surface and a bottom fluid impermeable surface and disposing a second sheet relative to said first sheet, said second sheet having a top fluid impermeable surface and a bottom surface. According to the method, the first sheet is attached to the second sheet in overlaying relation to create an interior inflatable portion, an opening is provided in the inflatable portion in which the method further includes the steps of: disposing a port in the opening interconnecting the exterior of the cuff with the interior of the inflatable portion; providing a slotted portion along an axial portion of the first sheet extending from the inflatable portion, the slotted portion being aligned with the port such that the port can be fitted within the slotted portion when the sleeve is wrapped about the limb of a patient; and treating one of the top surface and the bottom surface of the first sheet to reduce frictional effects when the axial portion of said first sheet is caused to be wrapped about the limb of a patient.

In one version, the top non-woven surface of the first sheet and the bottom fluid impermeable surface of the first sheet are defined by a static frictional coefficient and a dynamic frictional coefficient having value different from the static coefficient when the sleeve is one of inflated and deflated and wherein the treating step minimizes the difference between the static and dynamic frictional coefficients. Alternatively or in combination, the top non-woven surface and the bottom fluid impermeable surface of said first sheet are defined by a dynamic frictional coefficient that varies based on at least one of inflation and deflation of the sleeve, in which the surface treating step minimizes the variation in the dynamic frictional coefficient. In yet another embodiment, the surface treating steps increases at least one of the static and dynamic frictional coefficients between the contacting surfaces of said first sheet.

The treating step can include the step of removing surface oils impregnated in either surface of the first sheet. In one version, the oil removing step comprises the step of heating at least a portion of the cuff. In another version, the oil removing step comprises the step of washing at least a portion of the cuff.

The treating step can also preferably comprise the step of providing a surface texture to at least a portion of the fluid impermeable surface of the axial extension of the sleeve. In one version, this surface texture providing step includes the additional step of sanding at least a portion of a surface of the wrapped sleeve. In another version, the surface texture providing step includes the additional step of creating a surface pattern over at least a portion of one of the wrapped surfaces. The surface pattern can be created using at least one of welding, sanding, heating, stamping and extruding. According to one embodiment, the defined surface pattern can be substantially continuous applied over at least said portion of the fluid impermeable surface of the first sheet. In a preferred version, the surface texture is applied in a direction that is substantially axial relative to the sleeve.

In one version, the area of treatment extends from a seam defining the inflatable portion to the slotted portion. In another version, the area of treatment can locally extend along other portions of either or both contacting surfaces or over the entirety of each surface.

In one preferred version, the first sheet and second sheet are made from the same material. According to one version, the material enables recyclability. In one specific embodiment, the material selected is polypropylene.

According to yet another aspect, there is provided a blood pressure sleeve made by the process comprising the steps of: providing a first sheet having a top non-woven surface and a bottom fluid impermeable surface, and disposing a second sheet relative to said first sheet, the second sheet having a top fluid impermeable surface and a bottom surface. According to this method, the first sheet is attached to the second sheet in overlaying relation to create an interior inflatable portion. An opening is provided in the inflatable portion wherein the method further includes the steps of disposing a port in the opening interconnecting the exterior of the cuff with the interior of said inflatable portion, providing a slotted portion along an axial portion of the first sheet extending from inflatable portion, the slotted portion being aligned with the port such that the port can be fitted within the slotted portion when the sleeve is wrapped about the limb of a patient; and treating one of the top non-woven surface and the bottom fluid impermeable surface of the first sheet to reduce frictional effects when the axial portion of said first sheet is caused to be wrapped about the limb of a patient.

According to yet another aspect, there is described a blood pressure sleeve comprising at least one sheet having a top surface and a bottom surface and in which the at least one sheet is manipulated to form an inflatable interior portion. The inflatable interior portion includes an opening that receives a port fluidly interconnecting the interior of the inflatable portion with the exterior of the sleeve. At least one sheet including an axial sleeve extension having a slotted portion is aligned with the port such that the port can be fitted within the slotted portion when the sleeve is circumferentially wrapped about the limb of a patient wherein the top surface of the sheet is defined by a nonwoven side and the bottom surface is defined by a fluid impermeable side, and in which at least one of the non-woven and fluid impermeable sides of at least a portion of said first sheet is treated to reduce frictional effects between contacting top and bottom surfaces of the first sheet in a wrapped configuration.

An advantage realized herein is that the herein described sleeves can be used with blood pressure measurement systems in which results can be obtained either on the inflation or deflation portion of the measurement cycle.

Another advantage is that the herein described sleeves are relatively inexpensive to manufacture, but are reliable for their intended use.

Yet another advantage is that the sleeves discussed herein are more accurate than existing versions.

These and other features and advantages will be readily apparent from the following Detailed Description, which should be read in conjunction with the accompanying drawings.

BRIEF DESCRIPTION OF THE DRAWINGS

FIG. 1(a) is a perspective view of a blood pressure cuff made in accordance with an exemplary embodiment;

FIG. 1(b) is an exploded view of the blood pressure cuff of FIG. 1(a);

FIGS. 4(b) and 4(c) are graphical illustrations of load versus extension for an untreated blood pressure sleeve and various treated sleeves, respectively;

FIGS. 8-13 depict various exemplary surface treatments for reducing frictional effects between wrapped surfaces of a blood pressure cuff in accordance with the present invention.

DETAILED DESCRIPTION

Figure 2A:
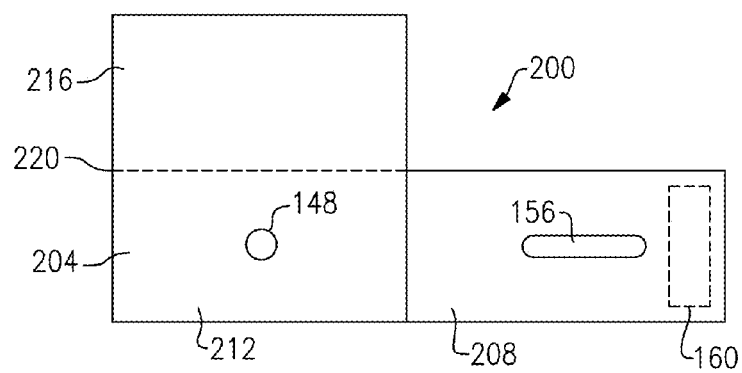
FIG. 2(a) is a top view of a blood pressure cuff made in accordance with another exemplary embodiment in a partially preassembled condition.

The following description relates to several exemplary embodiments of a single use or single patient blood pressure cuff or sleeve, including various surface treatments made to at least a portion of at least one wrapped surface. It will be readily apparent, however, that a number of other variations and modifications embodying the inventive concepts described herein are possible. In addition, certain terms such as "first", "second", "top", "bottom", "left", "right", "over", "beneath", "above" and "below" are used throughout in order to provide a suitable frame of reference with regard to the accompanying drawings. These terms, however, are not intended to be overlimiting, except, where so specifically noted.

Referring to FIGS. 1(a) and 1(b), there is shown a single use or single patient blood pressure cuff made in accordance with a first exemplary embodiment. The cuff 100 according to this version is made from a pair of planar sheets 110, 120, each made a highly flexible material that is recyclable and/or biodegradable. More specifically each sheet can be made from polypropylene, polyethylene or a combination of each material. By making the entire cuff 100 as described herein from the same material and in this embodiment, polypropylene, the cuff can easily be recycled following use. In accordance with a specific embodiment, the cuff can be classified as a category 5 recyclable product when the entire cuff, including the socket, is manufactured from approved types of polypropylene. Alternatively and in the instance in which the entire cuff 100 is made from polyethylene, the cuff can be classified as a category 2 or category 4 recyclable product, or as a category 1 recyclable product in which the cuff is made entirely from polyester. Moreover and even in the instance in which the cuff is not made entirely from a homogenous material, the herein described sleeve when incinerated does not release toxic and ozone depleting gases as in the instance of those blood pressure sleeves that contain polyvinylchloride (PVC). Still further, the sleeves can be further treated with an exemplary additive such as PPI Green Solutions Additive or Oxo-Degrader, in which the cuffs 100 are rendered biodegradable after a predetermined time period. In effect, the herein described cuffs are designed to be ecologically and environmentally friendly, whether through recyclability or biodegradability.

For purposes of the herein described cuff, the first sheet 110 is defined by a non-woven top side or surface 114 and a fluid impermeable bottom side or surface 118. The fluid impermeable bottom side 118 of the first sheet 110 is preferably defined by a film forming the surface of the sheet 110, which further includes a hook fastener portion 160, discussed infra, with the non-woven fabric being laminated to the film and forming the top surface of the sheet 110. The film in this embodiment has a thickness of about 0.002 to 0.008 inches, and preferably about 0.0025 to 0.0055 inches, and a weight of about 1.0 to 7.0 ounces per square yard, and preferably 1.2 to 4.6 ounces per square yard. Additionally, the non-woven fabric according to this embodiment will have a resulting weight of about 1.5 to 15.0 ounces per square yard, and preferably about 2.1 to 6.0 ounces per square yard. A creep elongation of the laminated fabric, as measured with a one inch by one inch test sample, loaded with five pounds over six minutes, should be less than about 0.0065 inches, and preferably less than about 0.0022 inches.

An intermediate transverse seam or seal 140 is formed at or near the middle of the length dimension of the herein described cuff 100, thereby dividing the cuff 100 into two adjacent sections, one section 130 of which is capable of inflation as described herein as well as an axial sleeve extension 170. The second sheet 120 is sized according to this embodiment in accordance with the inflatable portion 130 and defined by a fluid impermeable top surface 124 and a non-woven bottom side or surface 128. The peripheral edges of the first and second sheet 110, 120 are secured by means of ultrasonic welding, heat welding, RF welding, or other suitable means to create the interior inflatable portion 130 of the cuff 100. The interior surfaces of the inflatable portion 130 can be treated to reduce the incidence of frictional effects, such as lobeing and pillowing, as discussed in commonly owned U.S. Patent Application Publication No. 2012/0150051A1, previously incorporated herein in its entirety.

An opening 148 is formed in the first sheet 110 wherein a port supported upon a smaller sheet section 159, preferably made from the same material as the sheets 110, 120 is bonded to the interior of the sheet 110, and in which the port herein is defined by a socket 152 that extends through the opening 148 wherein a fluid tight seal is created about the periphery of the socket 152 within the opening 148. The socket 152 is defined by a relatively flexible circumferential or annular lip 158 and is also preferably formed of the same material (polypropylene) as those of the sleeve sheets 110, 120. A slotted portion 156 is formed in the opposite side of the cuff 100 in the axial extension portion 170 defined solely by the first sheet 110 wherein the major dimension of the slotted portion 156 is aligned with the extending socket 152 on the opposite side of the cuff 100. According to this embodiment, the slotted portion 156 and the socket 152 are provided at substantially the center of the width dimension of the cuff 100, as shown.

When wrapped, the slotted portion 156 is sized to accommodate the socket 152 and the slotted portion 156 is further sized to be wrapped only within a predetermined range of limb (arm) circumferences. The slotted portion 156, in combination with the extending socket 152, serves numerous functions. First and as noted, the slotted portion 156 will only accommodate a predetermined range of arm circumferences, in which the slotted portion 156 can be formed to accommodate a class of patient (e.g., a neonatal patient, a child, an adult, a large adult, etc). In addition, the slotted portion 156 further serves as a guide to wrapping the cuff 100 about the limb of a patient given that the socket 152 must be fitted within the slotted portion 156 when wrapped, as shown, for example in FIG. 4.

Figure 4:
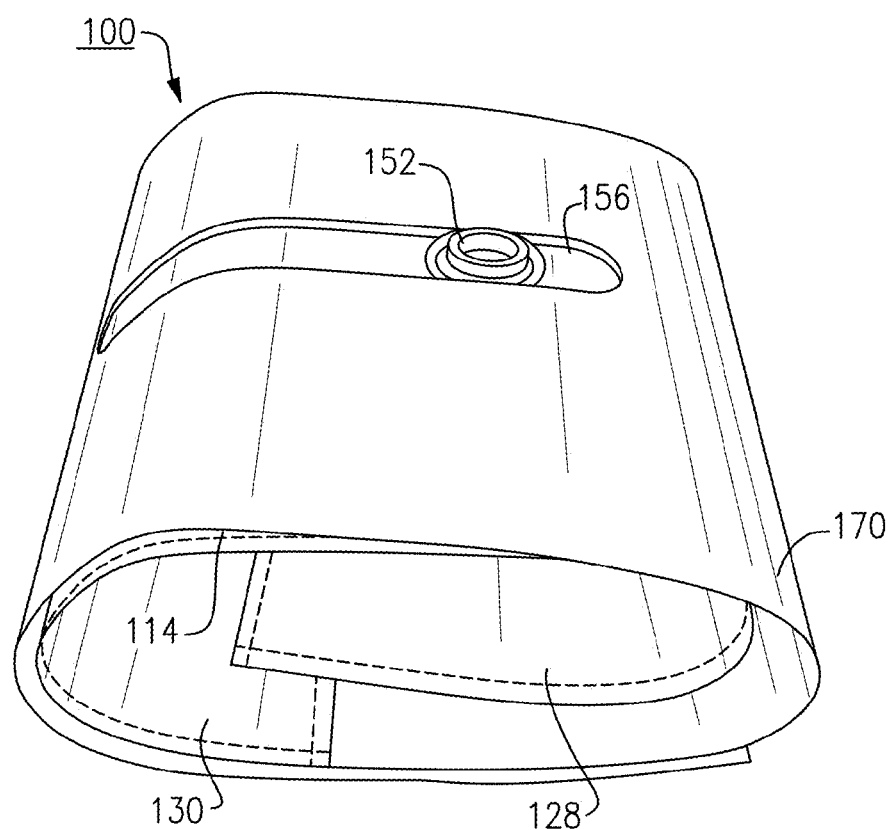
FIG. 4 illustrates the blood pressure cuff of FIG. 1(a) in a partially wrapped configuration.

Adjacent the opening 148 and the extending socket 152, the hook fastener portion 160 is provided on the exterior of the cuff 100 on the axial extension 170. More specifically and according to this embodiment, the hook fastener portion 160 is disposed on the bottom side 118 thereof adjacent the end of the cuff 100 opposite the inflatable portion 130. The hook fastener portion 160 is preferably made from the same material as that of the remainder of the cuff 100 and is bonded using appropriate means, such as heat sealing or welding. In this embodiment, the material of the cuff 100 on the non-woven sides of each of the first and second sheets 110, 120 is defined by a microstructure that creates adhesion with the hook fastener portion when the cuff 100 is wrapped. Due to the nature of this material, there is no need to provide a separate loop fastener portion to act as a closure means for the cuff 100, when the cuff is secured to the limb of a patient, as shown in FIG. 4.

A photograph taken under extreme magnification of a portion of the non-woven top surface 118 of the first sheet 110 is shown in FIG. 5(*a*). The non-woven microstructure of this surface provides a plurality of interstices for the hook fastener portion 160, FIG. 1(*a*), to engage and adhere. In this specific embodiment, the durability of the material of the first sheet 110 is affected with each attachment and subsequent removal of the cuff 100 from the hook fastener portion 160. This degradation of material influences the ability of the material to further adhere in those areas, thereby rendering the cuff 100 incapable of attachment after a finite number of uses. Depending on the material used, this finite number of uses could be made to be one or several.

Still further, the use of the slotted portion 156 and socket 152 permits the port to be flexibly located on the cuff 100 without interfering with the attachment thereof, including those involving the hook and loop fasteners. In fact, the hook fastener portion 160 can alternatively be positioned more conveniently along the exterior of the cuff. In this embodiment, the hook fastener portion can be positioned sufficiently inboard (that is, inboard relative to nearest lateral edge of the cuff) such that attachment can occur within the overlapping portion of the cuff that includes the slotted portion 156. By moving the attachment (fastener) portions more inboard, greater adhesion is achieved using less total surface area. Moreover and by selection of materials as in this embodiment, manufacture is simplified in that a separate loop fastener portion is not required given the inherent adhesive quality of the exterior sleeve material.

Figure 2B:
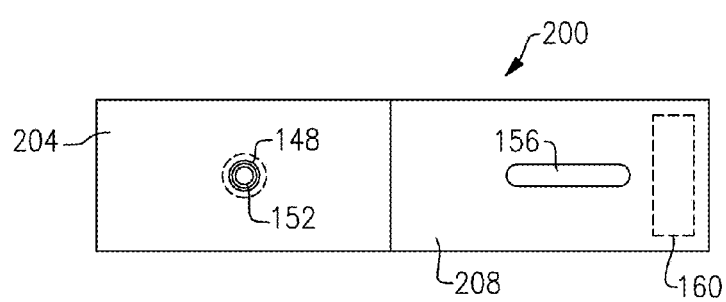
FIG. 2(b) is the top view of the blood pressure cuff of FIG. 2(a) shown in an assembled condition.

Alternative embodiments of a blood pressure cuff are provided in each of FIGS. 2(*a*) and 2(*b*) and 3(*a*) and 3(*b*). Similar parts are herein labeled with the same reference numerals for the sake of clarity. First and in the embodiment of FIGS. 2(*a*) and 2(*b*), a sheet 204 comprises a substantially L-shaped configuration generally having a lateral area 208, a central area 212, and a vertical area 216. The lateral area 208 includes the slotted portion 156 and the hook fastener portion 160, while the central area 212 includes the opening 148. The cuff 200 is formed according to this embodiment by folding the vertical area 216 under the central area 212 along a folded portion 220 of the sheet 204. A socket 152 is also extended through the opening 148 and attached to the sheet 204 as described previously. A bladder is then formed by sealing all of the peripheral edges between the central and vertical areas 212, 216, except for areas around the folded portion 220, which already forms a fluid impermeable barrier. The slotted portion 156 and the opening/socket 152, 148 are provided at substantially the center of the width dimension of the cuff 200, according to this embodiment, while the hook fastener portion 160 is also provided on the sheet 204 where the vertical area 216 is attached to the central area 212 of the sheet 204.

Figure 3A:
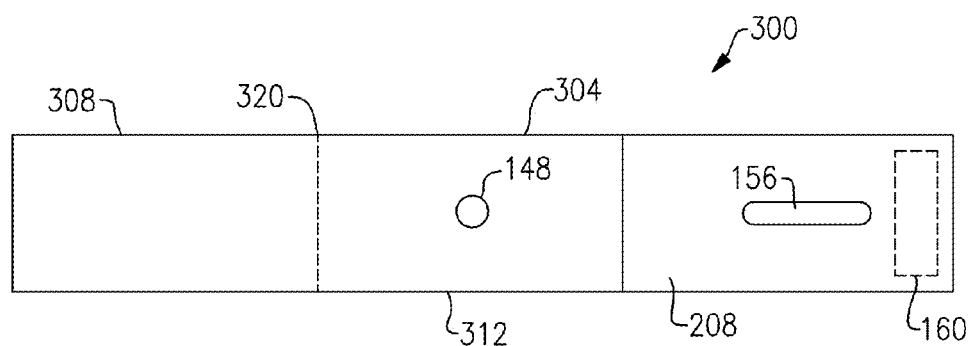
FIG. 3(a) is a top view of a blood pressure cuff made in accordance with another exemplary embodiment and in a partially preassembled condition.
Figure 3B:
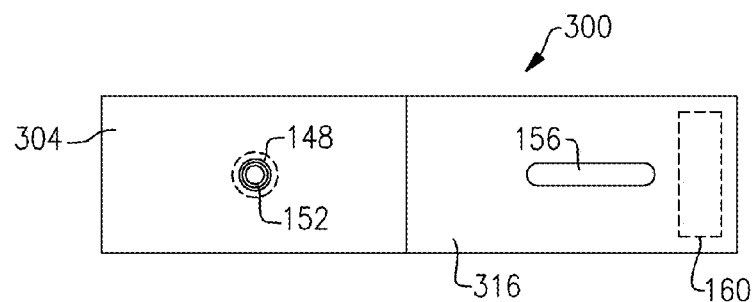
FIG. 3(b) is the top view of the blood pressure cuff of FIG. 3(a) in an assembled condition.

FIGS. 3(a) and 3(b) illustrate an additional embodiment of a cuff 300, in which the first sheet 304 comprises a substantially rectangular configuration generally having a left-lateral area 308, a central area 312, and a right-lateral area 316. The right-lateral area 316 includes the slotted portion 156 and the hook fastener portion 160, while the central area 312 includes the opening 148. Forming the cuff 300 according to this embodiment includes folding the left-lateral area 308 under the central area 312 along a folded portion 320 of the sheet 304. A socket 152 is also extended through the opening 148 and is attached to the sheet 304, as described above. Sealing all peripheral edges between the central and left-lateral areas 312, 308, except for areas around the folded portion 320, acts to form a bladder. The slotted portion 156 and the opening/socket 152/148 are provided at substantially the center of the width dimension of the cuff 300, while the hook fastener portion 160 is also provided on the sheet 304 where the left-lateral area 308 is attached to the central area 312 of the sheet.

Alternative sleeve or cuff embodiments are further described in U.S. Patent Application Publication No. 201210150051A1, previously incorporated by reference herein.

Advantageously, the cuff 100 can be wrapped in at least two separate wrapped orientations; that is, on either the left or right arm of a patient. A marker (not shown) can also be added to the cuff 100 in order to identify a patient or customize the cuff. Either wrapped orientation is made possible due to the "on-center" positioning of the port/socket and the slotted portion since the port is positioned in the same location on the limb of the patient in either instance. As such, neither orientation negatively affects the operation of the cuff in obtaining a blood pressure measurement from the patient. In addition, the port itself due to the symmetrical positioning thereof on the sleeve can also be used as an arterial marker, eliminating the need to add a specific marker to the cuff.

Referring to FIG. 4, the wrapped configuration of the blood pressure cuff 100 of FIGS. 1(a) and 1(b) are herein described in greater detail. For the sake of clarity, the limb of the patient is not shown in this view. First, the exterior or bottom surface 128 of the second sheet 120 of the sleeve 100 is placed in contact against the skin of the patient (not shown) with the inflatable portion 130 of the sleeve 100 being initially wrapped circumferentially. The non-woven side 114 of the inflatable portion 130 is consequently provided as an exterior surface exposing the socket 152, which is positioned over the brachial artery of the limb (not shown) in line with an marked arterial marker (not shown) of the cuff 100. The socket 152 is fitted into the slotted portion 156 of the first sheet 110 as the axial extending portion 170 of the sleeve 100 is circumferentially wrapped about the limb with the hook fastener portion 160 engaging the non-woven side 114 of the first sheet 110, forming a closure of the cuff 100 and securing the cuff 100 tightly to the patient (not shown) prior to inflation of the sleeve using pneumatic means (not shown) attached to the socket 152.

Figure 5A:
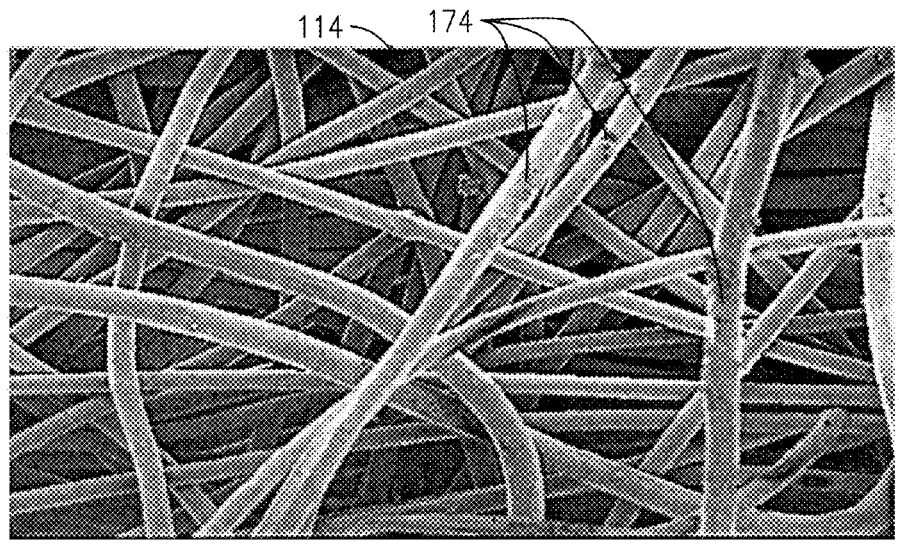
FIGS. 5(a) and 5(b) illustrate photographs taken under extreme magnification representative of a portion of the non-woven side and the fluid impermeable side, respectively, of a blood pressure cuff prior to treatment.
Figure 5B:
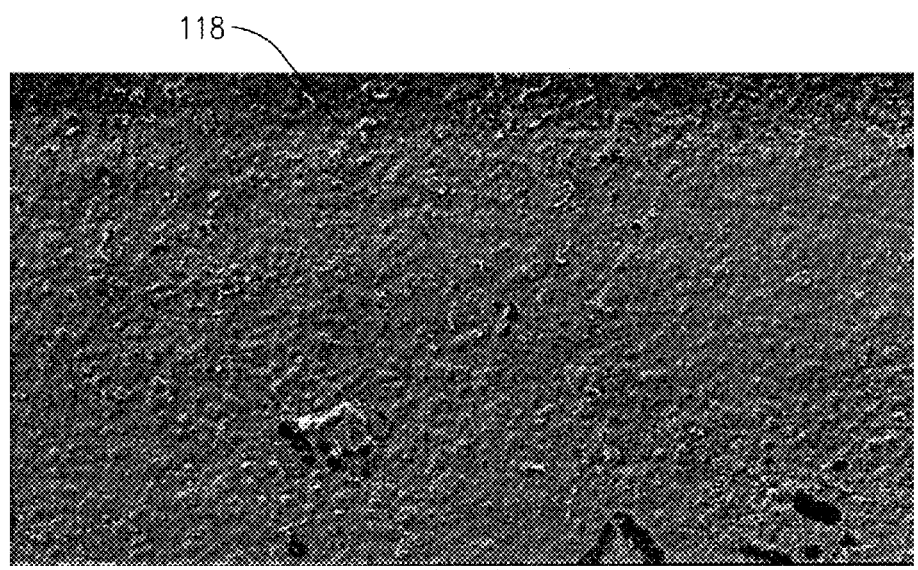

In this wrapped configuration and due to the length of the cuff 100, the hook fastener portion 160 engages the non-woven side 114 of the overlapping axial extension portion 170 of the sleeve that includes the slotted portion 156. In spite of the relative smooth surface provided by the fluid impermeable film side 118 of the first sheet 110, the sliding interaction between the film side 118 and the non-woven side 114 of the overlapping portions is inconsistent when the sleeve is inflated. Referring to FIGS. 5(a) and 5(b), there are presented photomicrographs of portions of the top and bottom surfaces 114, 118 of the first sheet 110. The polypropylene sheet 110 according to this exemplary embodiment and in its raw extruded form includes impregnated hydrophilic surface oils; as shown and labeled as 174 in FIG. 5(a) and also to the fluid impermeable film side 118, as shown under extreme magnification in FIG. 5(b). These oils are typically provided for fiber lubrication during the process of the non-woven side of the sheet 110, although certain sheets could be alternatively manufactured without requiring oil based lubricants.

Figure 4A:
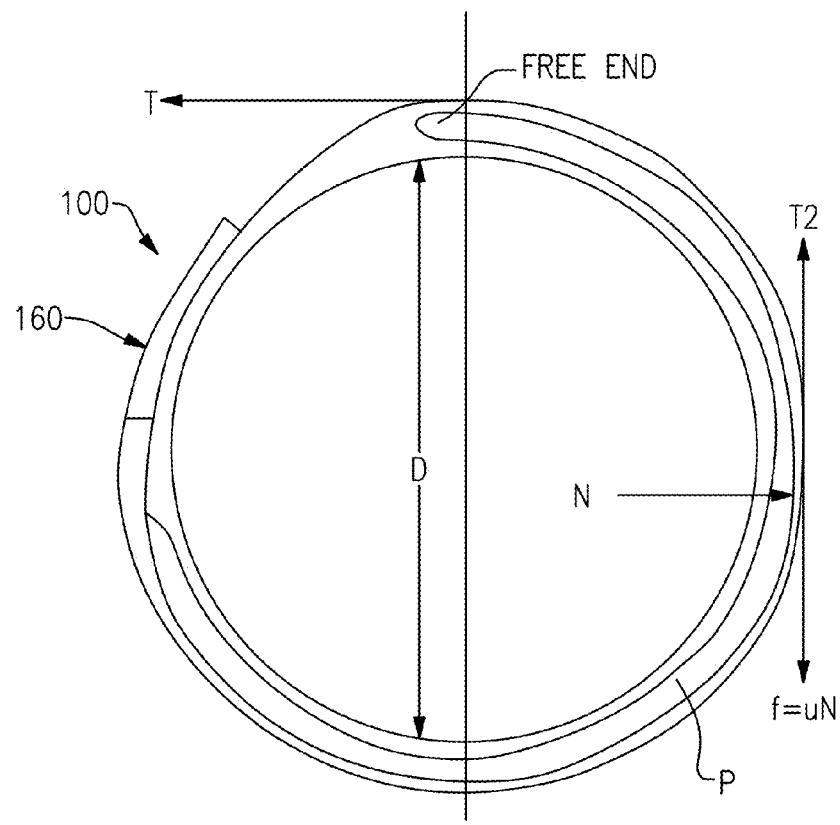
FIG. 4(a) depicts a free-body diagram of loads applied to the sleeve of FIG. 4.
Figure 4D:
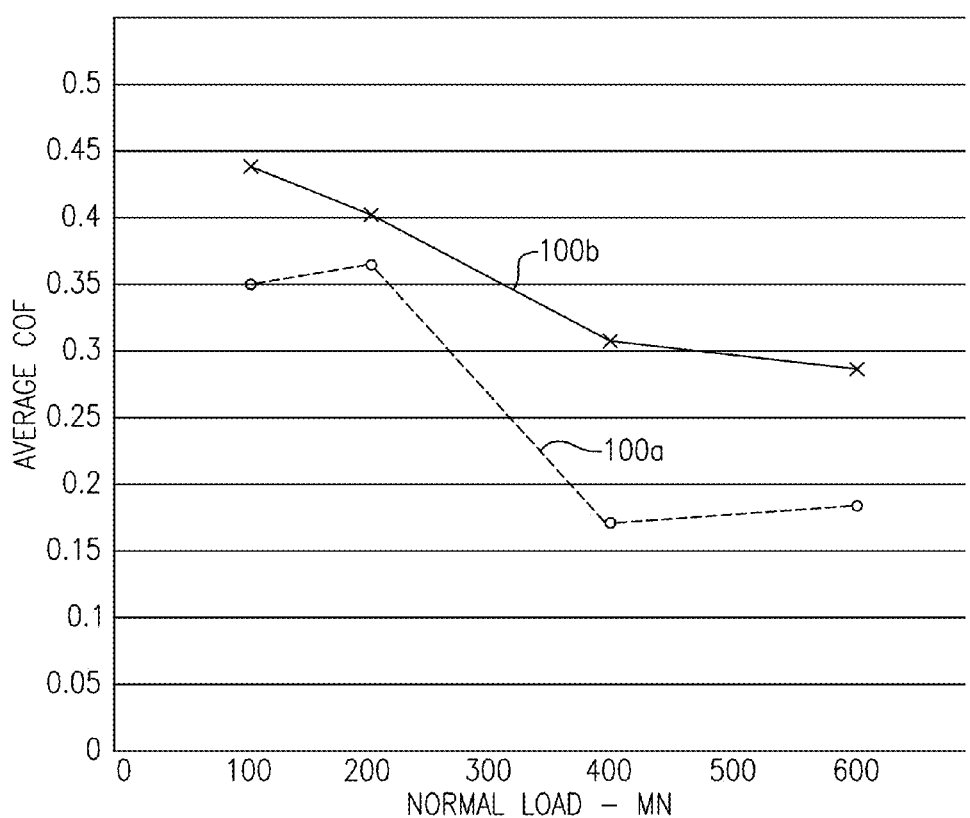
FIG. 4(d) is a graphical representation illustrating variable dynamic frictional coefficients for an untreated sleeve and a version according to an exemplary embodiment.

It has been determined that the wrapped cuff design as well as factors such as the presence of oil residue, humidity and others can contribute to a variation in frictional forces between the above noted surfaces. Reference is made to FIG. 4(a) which illustrates a free-body diagram representative of a untreated wrapped sleeve 100. Similar parts are herein labeled with the same reference numerals for the sake of clarity. As shown and prior to load, the surfaces are initially defined therebetween by a static frictional coefficient and under load by a dynamic frictional coefficient. As shown, inflation creates a normal load between the wrapped surfaces and this normal load increases with pressure. Side forces originate from the material hoop tension and the stretching of the material. These forces also increase as the cuff inflates. Two resultant issues, at a minimum, occur: First, the static coefficient of friction between two untreated wrapped surfaces is different than the dynamic friction coefficient under load. Second, the dynamic frictional coefficient has been determined to vary under load; that is, as the normal load (pressure within the cuff) changes. This variation is shown in FIG. 4(d) which compares an untreated cuff 100a with a cuff that has been sanded, by way of example, referred to on this graph as 100b. As clearly shown, the frictional coefficient varies dramatically as load is increased, as shown for cuff 100a.

Referring to FIGS. 4(b) and 4(c), the results of these variations are shown graphically. The effects of a relatively large difference between static and dynamic frictional coefficient are shown in FIG. 4(b), which further clearly illustrates a version of the "stick-slip" issue. The resulting delta based on the sleeve continually retracting and then reexpanding translates directly into overall and excessive signal noise, occasionally negating use in measurement systems.

It has been determined that certain treatments can be made to at least one of the wrapped surfaces of the cuff 100 such that the above noted differentials between the overlapping upper and lower surfaces 114, 118 are minimized. The results of exemplary surface treatments are shown graphically and by comparison according to FIG. 4(c) for a plurality of cuffs with a resulting large decrease in peak to valley "delta", as compared to the load extension graph of FIG. 4(b).

For the wrapped cuff design discussed herein and variants thereof treatment to at least a portion of one of the wrapped surfaces of the cuff 100 can be made to alleviate or minimize the above noted frictional effects. In one version, at least one of the contacting surfaces can be treated to reduce the differential between the dynamic and static frictional coefficients between the contacting non-woven and fluid impermeable surfaces of the axial extending portion of the sleeve. Alternatively or in combination, a surface treatment can be made to normalize "flatten" the dynamic frictional coefficient levels, see FIG. 4(d) between the surfaces over a range of loads (e.g., inflation pressures). According to yet another version or again in combination, at least one of the static and dynamic coefficients can be increased between the contacting surfaces, as depicted in FIG. 4(d), see curve 100b. For example, raising the static coefficient of friction between these surfaces tends to promote the adherence of these surfaces at the start of inflation. By raising one or both frictional coefficients (static and dynamic), the contacting surfaces behave more closely and consistently as a single layer.

Figure 6A:
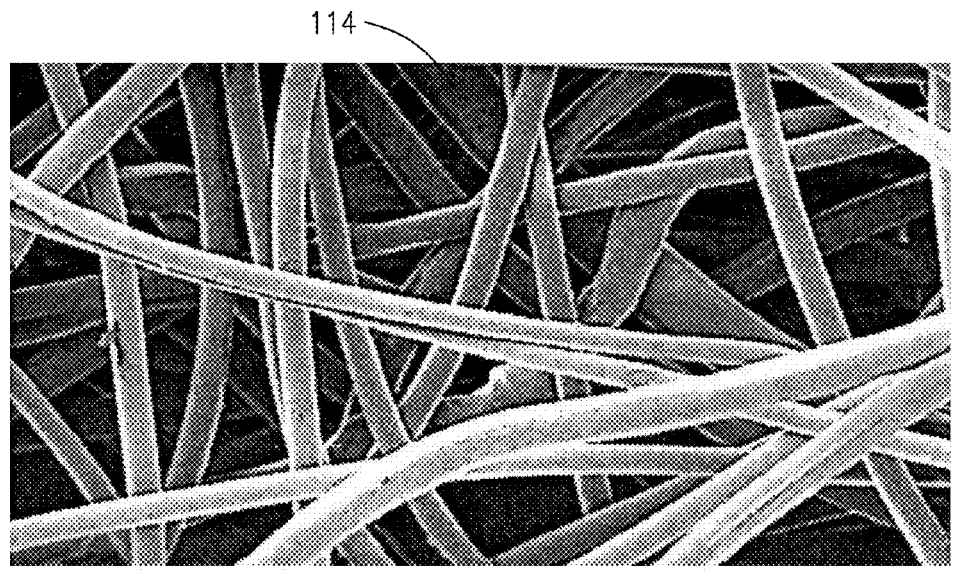
FIGS. 6(a) and 6(b) illustrate photographs taken under the same magnification of the non-woven side and the fluid impermeable side of the blood pressure cuff of FIGS. 5(a) and 5(b) following a washing step.
Figure 6B:
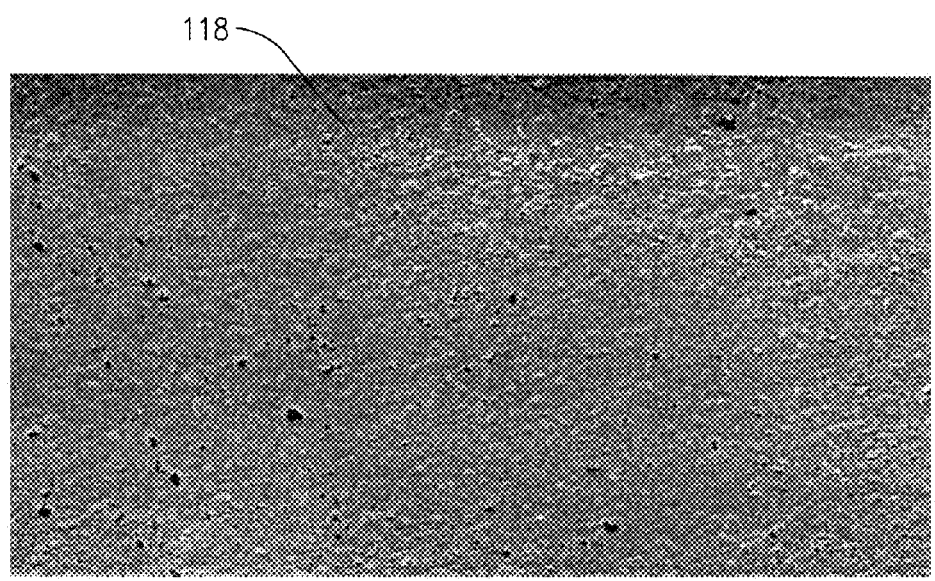

Various surface treatments are herein discussed that are effective in regard to the above-stated goals for reducing friction effects and the dichotomy between static and dynamic friction coefficients. For example and referring to FIGS. 6(a) and 6(b), the effects of washing or wiping at least a portion of the non-woven side 114 and the film side 118 of sheet 110 are respectively depicted in which a large percentage of the impregnated surface oils 172, FIG. 5(a), can be removed. The removal of these oils has been determined to effectively minimize variable frictional effects as discussed, including "stick-slip". As noted, alternative sheets can be fabricated that are not based on oil lubrication. This washing can be made locally to one portion of the sheet 110 or the entire cuff 100, prior to, during manufacture of the cuff or after manufacture. Alternatively, at least one portion of the surface of the cuff could be wiped, for example, with an alcohol based solvent or other suitable material. Similarly, the cuff 100 can be heated sufficiently to volatize or boil off at least a portion of the oil residue in order to provide added consistency in sliding contact between the contacting surfaces of the sleeve.

Figure 7A:
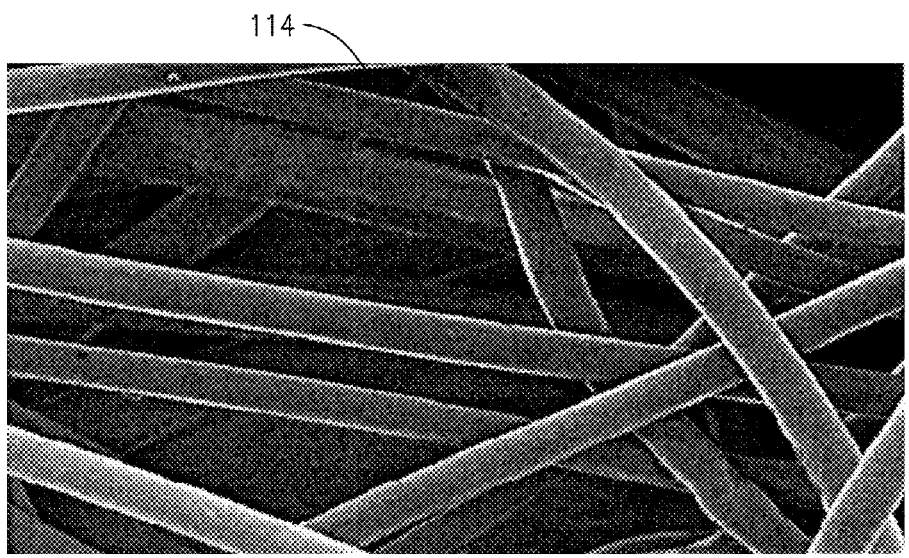
FIGS. 7(a) and 7(b) illustrate photographs taken under the same magnification of the non-woven side and the fluid impermeable side of the blood pressure cuff of FIGS. 5(a) and 5(b) following a surface treating step.
Figure 7B:
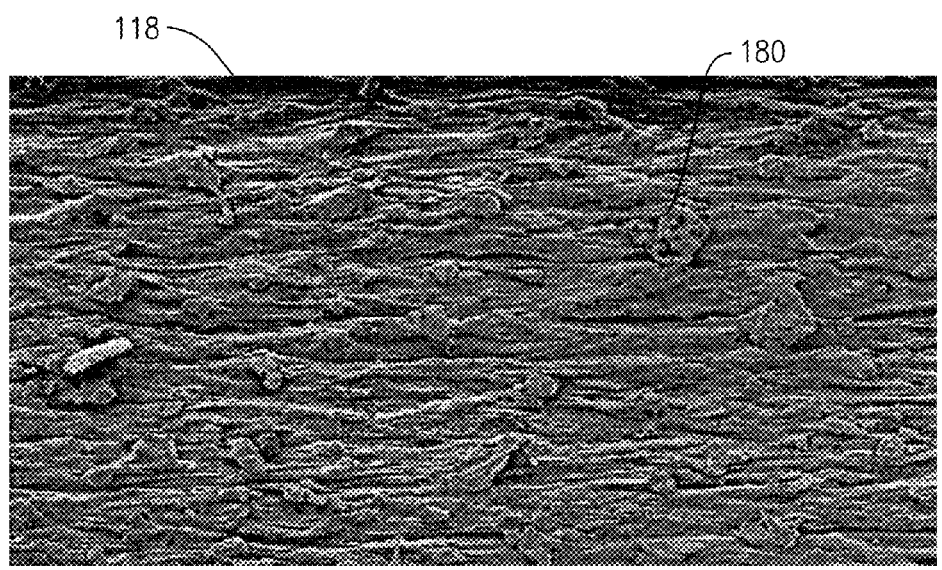
Figure 8:
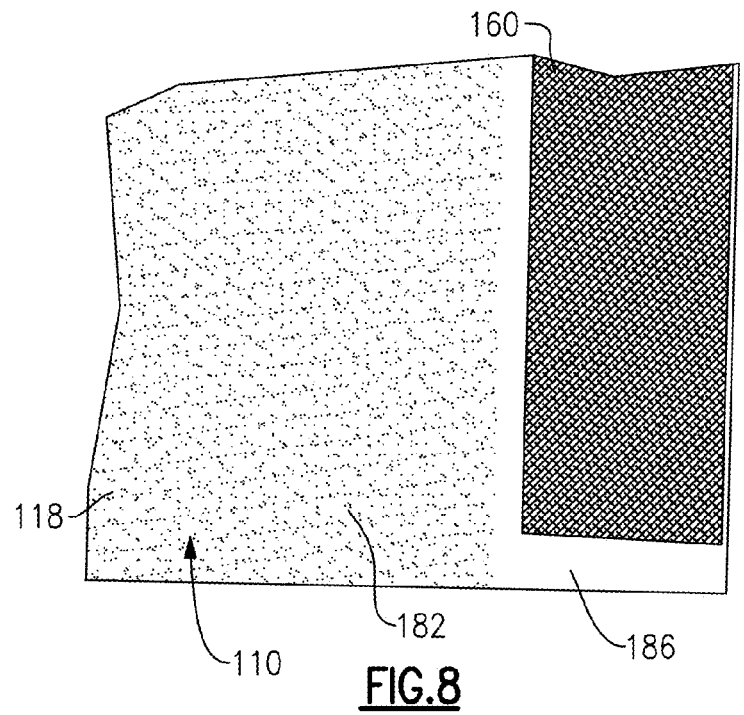

Referring to FIGS. 7(a) and 7(b) and according to an exemplary embodiment, at least one portion of the first sheet 110 can be surface treated by sanding. The effects of an exemplary sanding operation is shown in which a sanding wheel (not shown) is raised or lowered relative to each side of a linearly moving sheet. In particular and referring to FIG. 7(b), the application of a rotating sanding wheel on a web-driven sheet provides axial deformation on the film side surface 118 of the sheet 110 creating a preferred surface texture 180. In this embodiment, the sanded surface texture 180 compensates for the change in dynamic frictional coefficient by increasing at least one of the static and dynamic frictional coefficients. FIG. 8 illustrates the film side 118 of the sheet 110 in which a portion 182 of the surface has been sanded along a section extending from approximately the seam of the inflatable portion 130, FIG. 1(a), to the hook fastener portion 160 analogous to that shown in FIG. 7(b). As presented in FIG. 8, the amount of surface treatment needed can be nearly imperceptible to the naked eye. According to that figure and by way of contrast, the surface 186 adjacent the hook fastener portion 160 has not been sanded. To that end and according to the exemplary embodiment, it has been found that creating a surface roughness in the range of about 20 to about 500 microinches can be highly advantageous. The above results are somewhat surprising in that the film surface is somewhat roughened or exfoliated to produce the desired effect, as opposed to further smoothing the surfaces. As noted, the reasoning in creating the roughened surface effect is to produce greater consistency and accuracy during blood pressure measurement using this sleeve.

Figure 9:
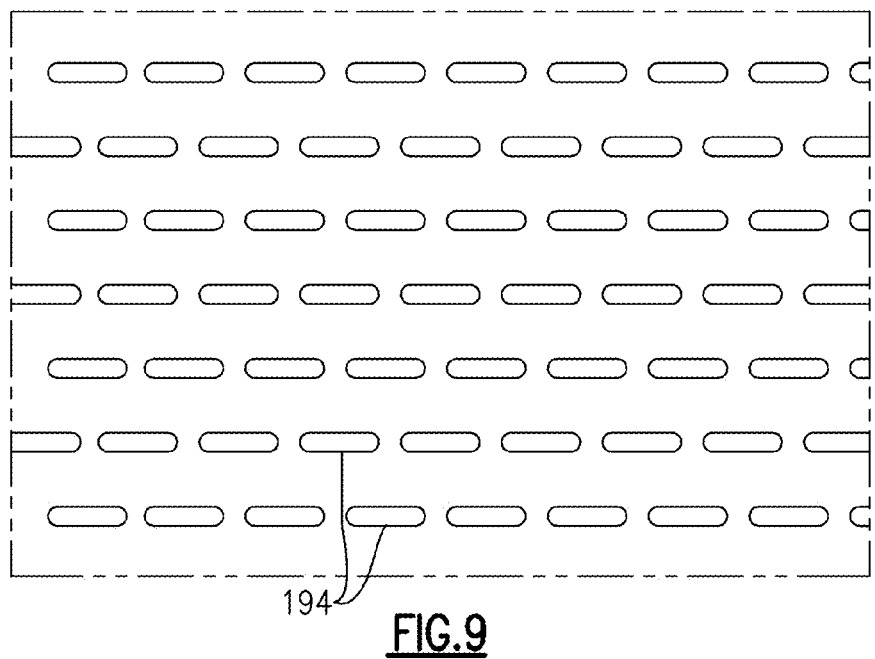
Figure 10:
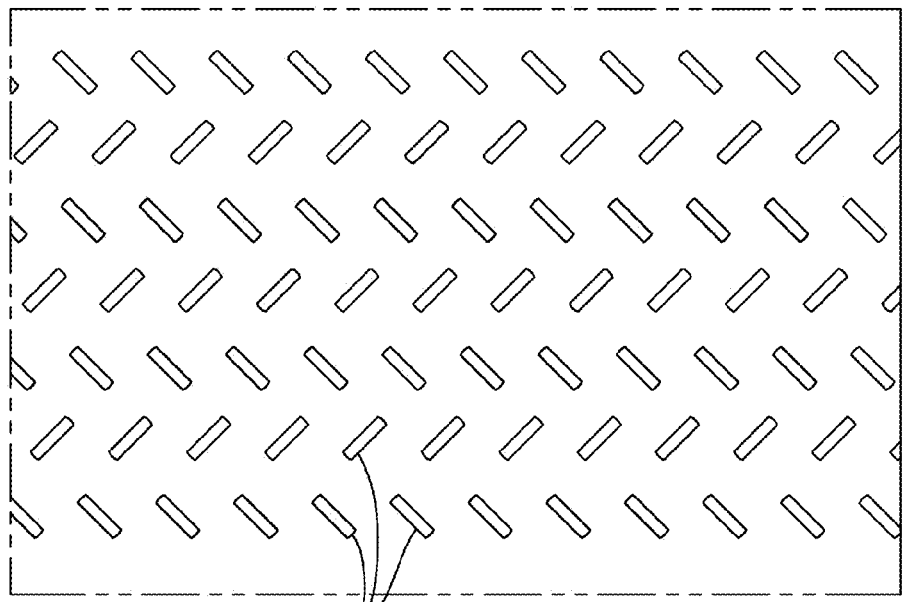
Figure 11:
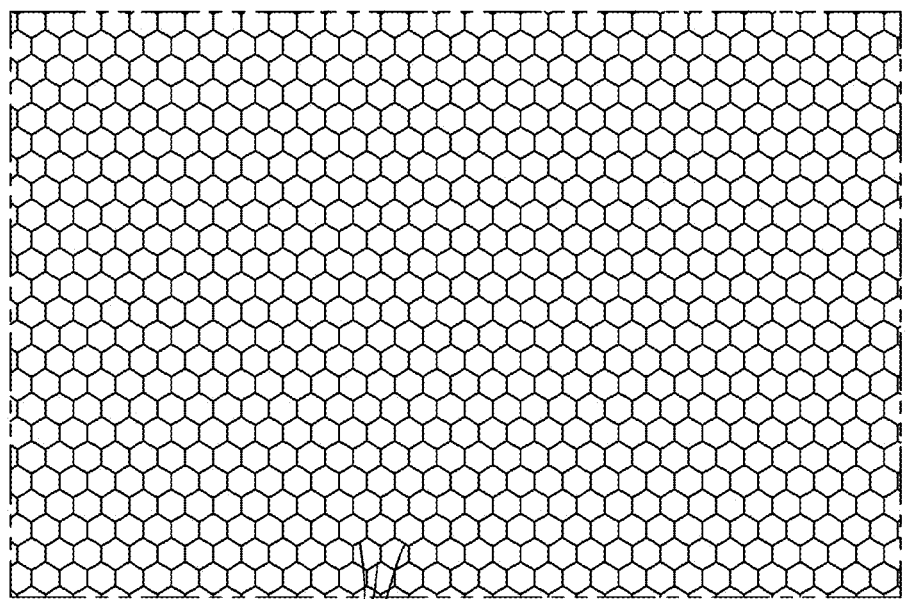

In like manner and referring to FIGS. 9-13, it has been surprisingly determined that creating other forms of textured film surface similarly minimizes the stick-slip effect discussed herein and improves the relative sliding movement between the overlapping non-woven and film surfaces during the entirety of a measurement cycle to thereby promote greater accuracy. This texturing can be created by various means, including various processes including stamping, heating, imprinting, sanding, and application of hot adhesive materials, among others. By way of example, FIG. 9 depicts an exemplary axial pattern 194 obtained through heat-staking. FIGS. 10 and 11 illustrates an exemplary surface patterns 195, 196 created using an ultrasonic horn or anvil placed on the sheet surface. Finally, FIGS. 12 and 13 illustrate a series of raised axial edges 197, 199, forming stripe-like features, each formed using melted adhesive applied using a plurality of spaced angled nozzles or a single nozzle with a plurality of spaced tips. As shown in each of the above examples, the patterns can be continuous or include intermittent spacings. Preferably, each of the surface patterns, like the sanding embodiment discussed above, are defined axially as opposed to transverse to produce a suitable texture for reducing frictional related effects.

An exemplary manufacturing assembly for the herein described cuff 100 preferably indexes a continuously-fed sheet 110 along a conveyor in which the surface texture, sanding or other effect can be disposed at a linear station; for example, a sanding wheel, in which the wheel is raised or lowered into contact with the sheet surface over a predetermined length as indexed for a specific type of cuff (adult, child, etc). The surface texture applying station can be provided along any part of the conveyor assembly or can be provided separately. Referring back to FIGS. 1(a) and 1(b), a preferred area of surface treatment is provided for purposes of the cuffs 100 described herein is between the seam 140 forming the interior inflatable portion 130 of the sleeve and the slotted portion 156. Alternatively, the area of treatment can be provided between the above-noted seam 140 and the hook fastener portion 160. Depending on the location of the surface treatment station, the entire bottom surface 118 of the first sheet 110 could be treated continuously as the sheet 110 is advanced though the assembly process or the entire sheet or finished cuff 100 could be washed, wiped or heat-treated prior to or following assembly.

PARTS LIST FOR FIGS. 1-13

100 cuff or sleeve
100a cuff
100b cuff
110 first sheet
114 top side or surface, non-woven
118 bottom side or surface, fluid impermeable
120 second sheet
124 top surface or side, fluid impermeable
128 bottom surface or side, non-woven
130 inflatable portion
140 seam or seal
148 opening
152 socket/port
156 slotted portion
158 circumferential lip
159 sheet, support socket
160 hook fastener portion
170 axial extension, sleeve
174 oil residue
180 texture 182 sanded portion
186 unsanded portion
194 axial pattern, surface
195 axial surface pattern
196 axial surface pattern
197 raised axial edges
199 raised axial edges
200 cuff
204 sheet
208 lateral area
212 central area
216 vertical area
220 folded portion
300 cuff
304 sheet
308 left lateral area
312 central area
316 right lateral area
320 folded portion It will be readily apparent that other modifications and variations are possible for those discussed in this application, including the following claims.

The invention claimed is:

1. A blood pressure sleeve comprising:
a first sheet having a top surface and a bottom surface;
a second sheet having a top surface and a bottom surface;
said second sheet being attached to said first sheet and defining an inflatable interior portion between the bottom surface of said first sheet and the top surface of said second sheet, said inflatable interior portion including an opening that receives a port fluidly interconnecting the interior of said inflatable portion with the exterior of said sleeve,
said first sheet including an axial extension having a slotted portion aligned with said port such that said port can be fitted within said slotted portion when said sleeve is circumferentially wrapped about the limb of a patient wherein the top surface of said first sheet is defined by a non-woven surface and the bottom surface is defined by a fluid impermeable surface, and in which at least one of said non-woven and fluid impermeable surfaces of at least a portion of said first sheet is treated to reduce frictional effects between contacting top and bottom surfaces of said first sheet in a wrapped configuration wherein at least a portion of one of the contacting top and bottom surfaces of the first sheet is treated such that at least one of the coefficient of static friction and the coefficient of dynamic friction between the top and bottom surfaces is increased from an untreated level.

2. A sleeve as recited in claim 1, wherein at least a portion of at least one of said contacting top and bottom surfaces of said first sheet is treated such that the differential between the static and dynamic frictional coefficients between said contacting surfaces is minimized.

3. A sleeve as recited in claim 1, wherein at least a portion of at least one of said contacting top and bottom surfaces of said first sheet is treated such that any typical variation in dynamic friction coefficient between said contacting surfaces is minimized.

4. A sleeve as recited in claim 1, wherein at least a portion of the fluid impermeable surface of said axial extension is exfoliated.

5. A sleeve as recited in claim 4, wherein the exfoliated portions of said axial extension of said sleeve are defined by a plurality of substantially parallel protrusions produced in the axial direction of said sleeve.

6. A sleeve as recited in claim 1, wherein at least a portion of the first sheet is at least one of washed and wiped.

7. A sleeve as recited in claim 1, wherein at least a portion of the first sheet is heat treated.

8. A sleeve as recited in claim 1, wherein at least a portion of said fluid impermeable surface is defined by a surface pattern disposed thereon, said at least one surface pattern being applied by one of sanding, extruding, stamping, heating and welding.

9. A sleeve as recited in claim 1, wherein the area of treatment of said fluid impermeable surface extends between a seam defining said inflatable portion and said slotted portion.

10. A sleeve as recited in claim 1, in which the axial extension includes a hook fastener portion for securing to said non-woven surface when said sleeve is wrapped and wherein the area of treatment of said fluid impermeable surface extends between a seam defining said inflatable portion and said hook fastener portion.

11. A sleeve as recited in claim 1, wherein said first and second sheets are entirely made from the same material.

12. A sleeve as recited in claim 1, in which the sleeve is configured to perform a blood pressure measurement during the inflation of the sleeve.

13. A method of manufacturing a blood pressure sleeve, said method comprising the steps of:
providing a first sheet having a top non-woven surface and a bottom fluid impermeable surface;
disposing a second sheet relative to said first sheet, said second sheet having a top fluid impermeable surface and a bottom surface;
attaching said first sheet to said second sheet in overlaying relation to create an interior inflatable portion;
providing an opening in said inflatable portion;
disposing a port in said opening interconnecting the exterior of said cuff with the interior of said inflatable portion;
providing a slotted portion along an axial portion of said first sheet extending from inflatable portion, said slotted portion being aligned with said port such that the port can be fitted within the slotted portion when the sleeve is wrapped about the limb of a patient; and
treating one of the top non-woven surface and the bottom fluid impermeable surface of said first sheet to reduce frictional effects when said axial portion of said first sheet is caused to be wrapped about the limb of a patient and in which a portion of one of the top non-woven and bottom fluid impermeable surfaces of the first sheet is treated such that at least one of a defined coefficient of static friction and a defined coefficient of dynamic friction between contacting top and bottom surfaces of the wrapped first sheet is increased from an untreated level.

14. A method as recited in claim 13, in which said surface treating step minimizes the difference between said static and dynamic coefficients.

15. A method as recited in claim 13, wherein the top non-woven surface and the bottom fluid impermeable surface of said first sheet are defined by a dynamic frictional coefficient that varies based on at least one of inflation and deflation of said sleeve, in which said surface treating step minimizes the variation in said dynamic frictional coefficient.

16. A method as recited in claim 13, in which said treating step includes the step of removing surface oils impregnated in either surface of said first sheet.

17. A method as recited in claim 16, wherein said oil removing step comprises the step of heating said first sheet.

18. A method as recited in claim 16, wherein said oil removing step comprises the step of at least one of washing and wiping said first sheet.

19. A method as recited in claim 18, wherein the area of treatment of said fluid impermeable side extends from a seam defining said inflatable portion to said slotted portion.

20. A method as recited in claim 18, wherein the area of treatment of said fluid impermeable surface extends from a seam defining said inflatable portion to a hook fastener portion provided at the end of said first sheet opposite said inflatable portion.

21. A method as recited in claim 16, wherein said first sheet and said second sheet are made from the same material.

22. A method as recited in claim 13, wherein said treating step comprises the step of providing a surface texture to at least a portion of a wrapped surface of the axial portion of said sleeve.

23. A method as recited in claim 22, wherein said surface texture providing step includes the additional step of sanding at least a portion of said fluid impermeable surface.

24. A method as recited in claim 22, wherein said surface texture providing step includes the additional step of creating a surface pattern over at least a portion of said fluid impermeable surface.

25. A method as recited in claim 24, wherein the surface pattern is created using at least one of welding, heating, stamping and extruding.

26. A method as recited in claim 24, wherein said surface pattern is substantially continuous over at least said portion of said fluid impermeable side of said first sheet.

27. A method as recited in claim 22, wherein said surface texture is applied in a direction that is substantially axial relative to the sleeve.

28. A blood pressure sleeve made by the process comprising the steps of:
   providing a first sheet having a top non-woven surface and a bottom fluid impermeable surface;
   disposing a second sheet relative to said first sheet, said second sheet having a top fluid impermeable surface and a bottom surface;
   attaching said first sheet to said second sheet in overlaying relation to create an interior inflatable portion;
   providing an opening in said inflatable portion;
   disposing a port in said opening interconnecting the exterior of said cuff with the interior of said inflatable portion;
   providing a slotted portion along an axial portion of said first sheet extending from inflatable portion, said slotted portion being aligned with said port such that the port can be fitted within the slotted portion when the sleeve is wrapped about the limb of a patient; and
   treating one of the top non-woven surface and the bottom fluid impermeable surface of said first sheet to reduce frictional effects when said axial portion of said first sheet is caused to be wrapped about the limb of a patient and in which a portion of one of the top non-woven and bottom fluid impermeable surfaces of the first sheet is treated such that at least one of a defined coefficient of static friction and a defined coefficient of dynamic friction between contacting top and bottom surfaces of the wrapped first sheet is increased from an untreated level.

29. A method as recited in claim 28, in which the sleeve is configured to perform a blood pressure measurement during inflation of the sleeve.

* * * * *